United States Patent
Mueller

(10) Patent No.: US 7,420,665 B2
(45) Date of Patent: Sep. 2, 2008

(54) OPTICAL DETECTION DEVICE WITH REDUCED LIGHT THROUGHPUT OSCILLATIONS

(75) Inventor: Beno Mueller, Ettlingen (DE)

(73) Assignee: Agilent Technologies, Inc., Santa Clara, CA (US)

(*) Notice: Subject to any disclaimer, the term of this patent is extended or adjusted under 35 U.S.C. 154(b) by 80 days.

(21) Appl. No.: 11/238,693

(22) Filed: Sep. 29, 2005

(65) Prior Publication Data

US 2007/0076204 A1    Apr. 5, 2007

(51) Int. Cl.
*G01N 21/00* (2006.01)
*G02B 6/00* (2006.01)

(52) U.S. Cl. .......................... 356/73.1; 385/12
(58) Field of Classification Search .............. 356/432; 385/66–68
See application file for complete search history.

(56) References Cited

U.S. PATENT DOCUMENTS 4,477,186 A    10/1984  Carlson ...................... 356/246
6,281,975 B1    8/2001  Munk .......................... 356/440
2001/0012429 A1*  8/2001  Wach et al. ................. 385/115
2006/0110101 A1*  5/2006  Lin et al. ...................... 385/16

FOREIGN PATENT DOCUMENTS

EP    0089157    9/1983
GB    2193313    2/1998

* cited by examiner

*Primary Examiner*—Tarifur R Chowdhury
*Assistant Examiner*—Tara S Pajoohi

(57) ABSTRACT

A method is provided to perform an optimized setting of an optical detection device, with the detection device comprising a first and a second waveguide, each having an end face adapted for emitting and receiving light and facing each other in a distance d, and an envelope which at least partially envelopes said distance d and which is adapted for at least partially guiding light between the end sides. The method comprises measuring of a transmission characteristic between the waveguides, which transmission characteristic shows at least one of a minimum and a plateau and which is dependent on the distance d, and setting of the distance d to a working point on the distance d in the minimum or plateau, wherein the variation of the transmission around the working point is low, accordingly the derivation of the measured transmission characteristic is low.

17 Claims, 2 Drawing Sheets

OPTICAL DETECTION DEVICE WITH REDUCED LIGHT THROUGHPUT OSCILLATIONS

BACKGROUND ART

The present invention relates to an optical detection device.

The optical detection of components in fluids is well known in the art. Chemical separation techniques such as liquid chromatography are generally followed by further separation or detection steps. Measuring of concentrations of interesting components being enriched in an elute, e.g. may be detected by application of techniques applying physical phenomena that don't interfere with the chemical fluidic system and which don't disturb the "shape" of the component's concentration peak. If chemical separation is performed in a cylindrical chromatography column one might wish to proceed using a cylinder shaped detection device in order to prevent disturbing of the "plug-shape" of the separated components. Optical detection for measuring physical properties such as concentrations accordingly goes perfect together with the before mentioned requirements.

In order to perform such optical detection, an optical detection device generally comprises a measuring chamber or cuvette containing the fluid to be analyzed, a light emitting and a light receiving device. One may perform transmission measurements by guiding light through the fluid and measuring the light throughput, under consideration of optical laws such as Beer's law, which is known to those skilled in the art. Generally one can say that the reliability on optical measurement is based on the precision of controlling and detecting the light input into the fluid, its throughput and its output—parameters that depend on the characteristic such as surface design or length of the measuring chamber or cuvette, respectively.

In U.S. Pat. No. 6,281,975, Munk describes a capillary flow cell with protruding bulb ends providing a high light throughput entrance window for the cell, aiming for an improved sample illumination.

UK 2,193,313 A to Lefebre and Schirmer refers to a spectral analysis apparatus and method for measuring the spectral absorbance of fluid samples, focusing on the adjustment of the light path through the sample to optimize the amount of light absorbed by the sample, intending to enable absorbance measurements over a wide range of absorptivities and concentrations.

EP 0,089,157 to Le Febre discloses an optical detector cell for determining the presence of a solute in a sample fluid, for the particular application in miniature chromatographic and micro spectroscopic applications. An optical flow path which is parallel to the fluid flow path is provided, allowing maximizing of the sample corresponding to a fixed sample volume, whereby the ability results to measure low threshold concentrations in solutes.

U.S. Pat. No. 4,477,186 to Carlson refers to a photometric cuvette for optical analysis of through flowing media, designed for the measurement of minimum sample amounts.

SUMMARY OF THE INVENTION

It is an object of the invention to provide an improved optical detection of fluids.

According to an embodiment of the present invention a method is provided which permits performing an optimized setting of an optical detection device which comprises a pair of corresponding waveguides and an envelope or measuring chamber, respectively, which is adapted to be filled with or flown through by the fluid of interest. The corresponding waveguides are located in a distance d and facing each other so that light being emitted by the one of the waveguides has to be transmitted through the distance d to become received by the other one of the waveguides. Thus, measurements between the waveguides result in a transmission characteristic which depends on the distance d and on the reflecting properties of the reflecting enveloping material as well as the absorption properties of the fluid or liquid (solvent plus analytes), respectively, in between the waveguides. The curve mapping the transmission characteristic is an oscillating decay curve showing an optimal working point for transmission measurements. Variations in measuring results due to changes of the working conditions such as temperature changes of the enveloping material or the fluid are remarkably lowered in the region of the working point, thus the reliability in the measurements is increased due to an optimized precision. Setting of the working point accordingly means defining the length of the actually through flown measuring chamber, so an optimal relation between chamber length and light throughput is obtained.

A further embodiment of the present invention is a detection device which is provided to perform an optimized optical analysis of fluids, applying the method of setting a working point.

Another embodiment of the present invention is a detection device with an envelope or fluid chamber, respectively, which is provided with a texture at its inner or outer surface. So the light which is emitted by the emitting wave guide and which is transmitted to the receiving wave guide is reflected and refracted more frequently than in a smooth envelope. Thus, the enveloped distance between the two fibers is well illuminated, thus the sensitivity of the device with respect to parameters influencing the measurement negatively is reduced, which effect can be increased by applying the method of setting a working point.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

DETAILED DESCRIPTION OF THE PREFERRED EMBODIMENT

In order to perform analysis of components in fluids one often makes use of the simple optical measurability of physical parameters which depend on chemical and physical parameters of components in the fluid. In particular for analysis of components in fluids such as eluents in chromatographic processes which comprise eluted components in different concentrations due to previously performed chromatographic applications, one may wish to detect the interesting components without disturbing the process. Optical detection techniques may be based on the measurement of transmission, absorption or reflection: The amount of light directed into a sample splits in an absorbed quota, a transmitted quota and a reflected quota.

Performing an optical detection generally comprises a chamber for isolating the interesting fluid, said chamber being in contact with a light emitting source, a light transmitting device and a light receiving device, which light receiving device is needed to perform the differential calculation which relies on the above relationship between the three quotas.

Figure 1:
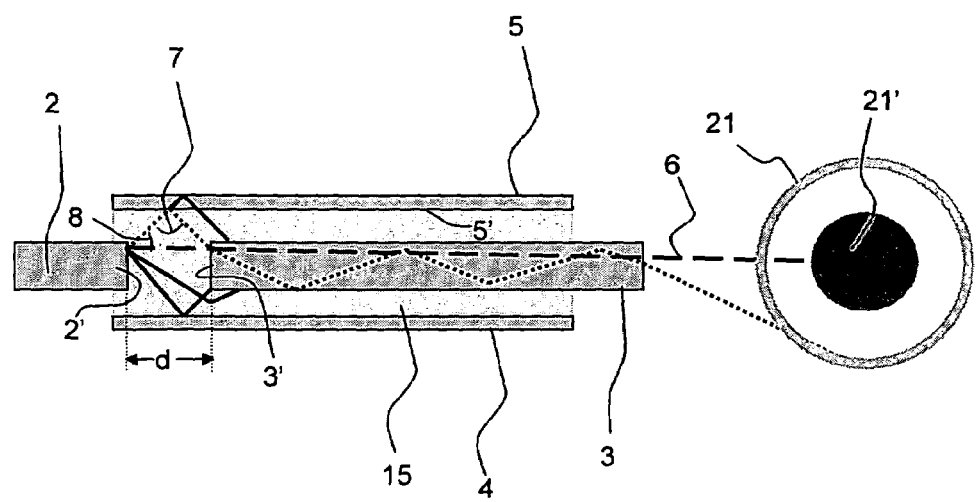
FIG. 1 shows the detection device comprising an envelope with a smooth surface.

FIG. 1 shows a detection device 1 to perform transmission measurements. It comprises a first waveguide 2 for emitting light and a second waveguide 3, for receiving light. The waveguides 2,3 have end faces 3',2' which are facing each other in a distance d. The distance d is enveloped by a capillary 4, so the light being emitted by the waveguide 2 is guided along the distance d inside the capillary to the light receiving waveguide 3. Advantageously, the capillary 4 is made of a material such as an amorphous fluoropolymer or quartz or a combination of both that provides a total reflectance of the light inside the capillary 4, making sure that losses of light through the envelope is prevented. As depicted above, the envelope in FIG. 1 is a capillary 4, herein serving as flow-through chamber, but a tube or any other suitable encasement might serve as envelope too, being filled with fluid batch-wise or by the flow-through mode. The using mode depends on the specific design of the envelope in the particular embodiments.

The waveguides 2, 3 could be fibers such as quartz fibers. One could use a single fiber as well as a bundle of fibers, with the endings of the fibers being even cut herein, thus forming the end faces 2',3', which generally cause emerging of a diffuse light beam. Of course, otherwise shaped end faces of the fibers such as spherically or, lens shaped end faces may be used, too. The composition of the light beam with respect to the wavelengths depends on the light source, so one may generate a monochromatic or a polychromatic light beam to be transmitted along the distance d. Light sources generally might be diodes, diode arrays, incandescent lamps, deuterium lamps and mercury low-pressure or high-pressure discharge lamps or any other suitable lamp. It might be noticed, that the total reflectance of light requires that the outer surface 5 is free from soiling such as grease due to touching of the surface: Herein, an interface quartz to air or an interface quartz to amorphous fluoropolymer permits total reflection. Other options to provide total reflection inside the envelope may comprise the coating of said envelope with a suitable reflecting substance or dye.

Optical measurements are generally performed under the consideration of certain optical laws, which rely on parameters such as the length of the path which has to be passed by the light: In FIG. 1, the light is transmitted through the fluid 15 inside the capillary 4, which light or light beam, composed of a plurality of electromagnetic waves or "light rays", is refracted at the inner surface 5' of the envelope and it is reflected at the inner surface 5' of the envelope and reflected at the outer surface 5 of the envelope, so that there exists a plurality of refractive and reflecting angles 7, which lead in a given relation of capillary 4—or envelope generally—and waveguides to a certain behavior of the transmitted light rays due to geometrical conditions. Said geometrical conditions refer in particular to the distance d, which is the relevant dimension for an envelope of cylindrical shape.

When the distance d of the end faces 2',3' is zero, (d=0), the complete amount of light emitted at the end face 2 is transmitted, thus the transmittance T from the emitting waveguide 2 to the receiving waveguide 3 is T=1, whereby reflection losses at the waveguide 2,3/liquid 15 interfaces are being neglected here. Moving the waveguides 2,3 and 3 along the longitudinal axis of the capillary 4 in opposite directions leads to separation of the end faces 2,3 and thus to an increase of the distance d, which leads to a loss of the light throughput along said distance d because of the following:

When the light rays emerge the end face 2, numberless light ray cones enter the enveloped space which is the distance d herein, each ray cone being comprised of light rays having different beam angles 8 provoking different reflective and reflecting angles 7. Only light rays 6 being emitted in the center of the cone can be transmitted directly without being reflected or refracted. Said ray cone is symmetrically at the center of said end face, but not in the outer areas. Simplified, one might say that the light emitting waveguide 2 is a light spot source, the reflection angle tan α being then the waveguide radius divided by the distance d. So, there are light rays that can't be received by the waveguide 3 since the fixedly given angle of the light ray cone which passes the distance d without reflections and which hits the end face 3' directly becomes smaller and smaller and, hence, the radiant energy density is reduced. This means, that with increasing distance d the transmission T decreases. FIG. 1 shows an image of this phenomenon, leading to an illuminated circle 21 with decreasing diameter, as it is projected on a screen. One could use a or camera chip as well.

At a greater distance d, which is exemplarily indicated in FIG. 1, the light rays being reflected at the inner and outer capillary surfaces 5, 5' with the greatest angles 7 hit the receiving end face 3' of the waveguide 3 again and the throughput or transmission of the system raises again. On the screen behind the waveguide 3 a new illuminated ring 21' with greatest diameter arises. With increasing distance d of the end faces 2',3' the phenomenon recurs, thus plotting of the measurement points obtained by transmission measurements to create a graph—see FIG. 3—shows a transmission characteristic which represents the oscillating transmission function 12 of the system. Generally, the system of illumination rings 21, 21', too, can be projected on a screen or on camera.

In order to perform an optimized setting of an optical detection device 1, a method is applied as described in the following: Generally, the method is based on a transmission characteristic which could be obtained by transmission measurements performed in an optical detection device according to an embodiment of the present invention, whereby the optical detection device can be filled with a gas, air or a liquid.

Figure 3:
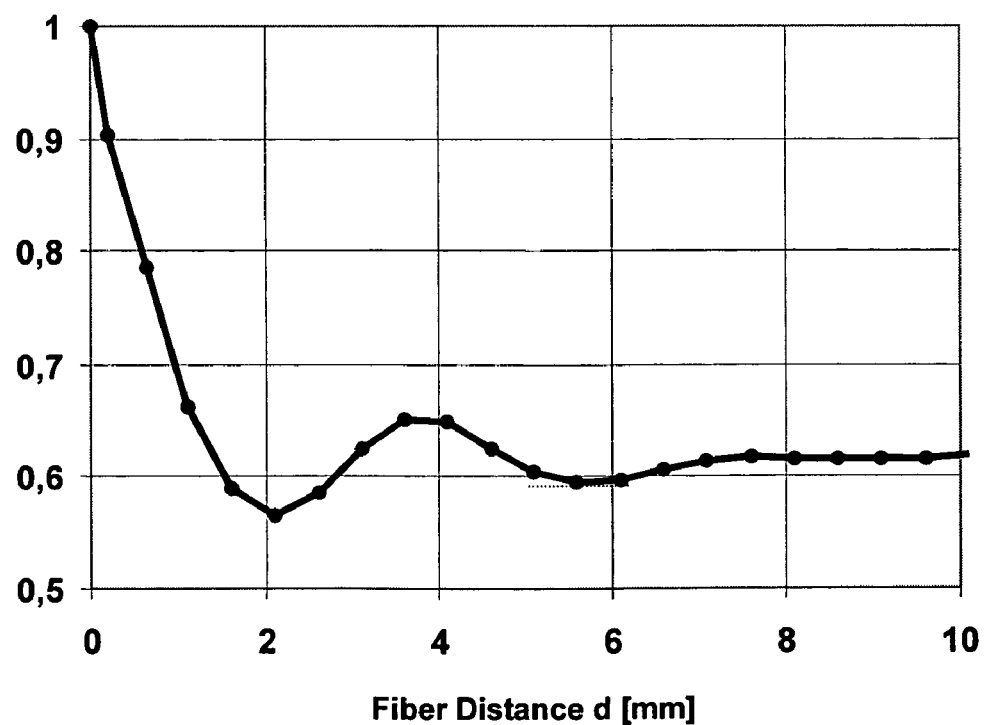
FIG. 3 shows an experimental data plot depicting the transmission characteristic for the detection device of FIG. 1.

In the following the transmission characteristic as show in FIG. 3 is taken into consideration exemplarily. The transmission characteristic 12 is an oscillating decay curve comprising minima 13 and transiting into a plateau 14. The minimum 13' which is depicted in FIG. 3 shows the last minimum before the plateau area 14 is reached. This minimum 13' represents the transmission results as being received for a certain distance d, so the minimum 13' represents a working point at which the variation of the transmission is low when the parameters that effect the transmission vary and, hence, the derivation of the measured transmission characteristic is low at said working point.

Generally said, setting the waveguides to said working point on the distance d in said minimum or plateau provides an optical detection device suitable to perform reliable transmission measurements with little variation. The setting of the waveguides may be performed directly when the manufacturing of the optical detection device is done, or it could be done by the user later on. This option is based on the movability of at least one of the waveguides until the setting is carried out; afterwards final fixing of the movable waveguide or of both waveguides, respectively, could be done.

Figure 2:
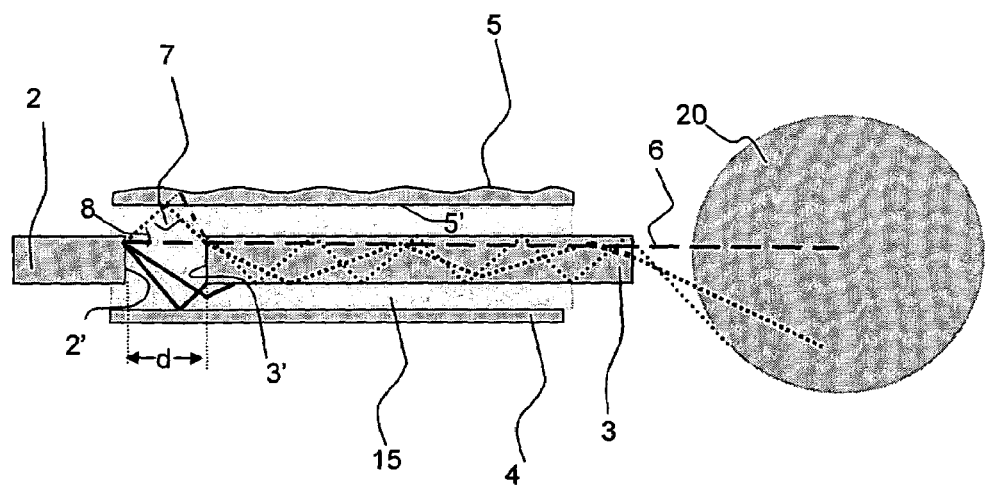
FIG. 2 shows the detection device comprising an envelope having a textured surface.

In FIG. 2 another embodiment of the present invention is shown: The herein depicted detection device 10 is adapted to perform optical analysis, too. It is designed as the detection device 1—see FIG. 1—except of the characteristic feature, that the envelope, being a capillary 4 herein, has an outer surface 5 with a texture.

Generally, any device serving as envelope such as a tube, capillary or the like, has an inner and an outer surface providing a plurality of refractive angles and reflective angles even when said surfaces are smooth and clean. Putting a texture on the inner or the outer surface or both of them provides an less regular refractive and reflecting of the light rays emerging the end face of the emitting wave guide, which leads to an more mixed distribution of reflective and refractive angles, thereby enhancing the homogeneity of the illumination of the distance d due to mixing of the light ray reflecting and refractive angles. The increased number of reflecting and refractive angles permits the increased receiving of light rays by the light receiving end face, since the angle with which the light ray is reflected is responsible for the hitting of the end face and the succeeding transport of said light ray along the waveguide. The homogeneously illuminated distance d—containing the fluid 15—leads to the ring 20 as shown in FIG. 2.

Thus, the above explained ring system becomes more diffuse and the oscillations in the transmission characteristic are smoother than they are in an identical optical detection device with smooth inner and outer surfaces of the envelope. After all, the smoothed transmission curve points out, that the optical detection device which has a textured inner or outer surface—or the both—is less sensitive to refractive index variations of the solvents, to geometrical changes of waveguide and envelope, temperature induced variations.

The texture could be one of an embosses pattern of helical shape, a rippled or ragged pattern or any irregular pattern which is aligned with the envelope. Analogous to the detection device with a smooth inner and outer envelope surface, the textured envelope is made of a material such as an amorphous fluoropolymer or quartz that provides a total reflectance of the light inside said envelope. After all, one may additionally apply the above depicted method of setting the waveguides to a working point, which means a further optimization of the reliability on the transmission measuring results due to further reduction of transmission variation based on parameters like temperature of the fluid and the like.

Furthermore, the optical detection devices according to any embodiment of the present invention could be part of an optical detection system which could be suitable to analyze a fluid stream with changing concentrations of one single component or to analyze fluid streams with different concentrations or concentration peaks of different interesting components. Performing these or comparable applications is feasible by connecting two or more optical detection devices in series. Therefore, one might connect the envelopes or chambers, respectively, to design a flow path which permits the flowing of the fluid from the first to the last chamber. In this case, it is advantageous to provide each of said chambers with an extra emitting and an extra receiving waveguide. Each of which corresponding pair of waveguides could be set according to the above method. One might wish to connect chambers having different lengths and, hence, having different distances d, in order to focus on different component concentrations in the fluid which specifically effect the refraction index. Highly concentrated components could advantageously be detected by use of short chambers or envelopes, respectively, having short distances d, where as low concentrations could be detected by use of long chambers or envelopes, so a combination of both long and short envelopes permits the detection of different concentrations.

What is claimed is:

1. A method to perform a setting of an optical detection device, which detection device comprises a first and a second waveguide, each having an end face adapted for emitting and receiving light and facing each other in a distance d, and an envelope at least partially enveloping the distance d and being adapted for at least partially reflecting and guiding emitted light between the end faces, the method comprising:
   measuring a transmission characteristic of a fluid between the waveguides while varying the distance d, wherein the transmission characteristic shows at least one of a minimum and a plateau, and
   setting the distance d to a working point in said minimum or plateau,
   wherein a variation of the transmission around the working point is low, accordingly a derivation of the measured transmission characteristic is low.

2. The method of claim 1, comprising:
   moving of the waveguides along a longitudinal axis of the envelope towards each other or in opposite directions, thereby varying the distance d.

3. The method of claim 1, comprising:
   measuring of the transmission characteristics by performing transmission measurements between the waveguides for a plurality of distances d under maintenance of the device parameters.

4. A detection device adapted to perform optical analysis, comprising:
   a first and a second waveguide, each having an end face adapted for emitting and receiving light and facing each other in a distance d, and an envelope at least partially enveloping the distance d and being adapted for at least partially reflecting and guiding emitted light between the end faces,
   wherein the distance d is set, based on a previously derived measurement of a transmission characteristic of a fluid between the waveguides while varying the distance d, which transmission characteristic showing at least one of a minimum and a plateau, to a working point within the minimum or the plateau,
   wherein the variation of the transmission around the working point is low, accordingly the derivation of the measured transmission characteristic is low.

5. The detection device of claim 4, wherein the envelope is made of a material such as an amorphous fluoropolymer or quartz that provides a total reflectance of the light inside said envelope.

6. The detection device of claim 4, wherein the envelope is coated with a reflecting substance which substance is a fluoropolymer or dye.

7. The detection device of claim 4, wherein the envelope has an longitudinal axis and wherein at least one of the first and the second waveguides is movable along said longitudinal axis.

8. The detection device of claim 4, wherein the end faces are spherically domed or lens shaped.

9. The detection device of claim 4, comprising a light source providing the light being emitted by the waveguide, said light source is at least one selected from the group consisting of: diode, diode array, incandescent lamp, deuterium lamp, mercury low-pressure or high-pressure discharge lamp, and any other suitable lamp.

10. A detection device adapted to perform optical analysis, comprising:
    a first and a second waveguide, each having an end face adapted for emitting and receiving light and facing each other in a distance d, and an envelope at least partially enveloping the distance d and being adapted for at least partially guiding light between the end faces, wherein the envelope has an inner and an outer surface providing a plurality of refractive angles and reflection angles, at least one of the inner and an outer surface having a pattern for increasing said plurality of refractive angles and said plurality reflection angles, thereby providing a homogeneous illumination of the distance d wherein the distance d is set, based on a previously derived measurement of a transmission characteristic relying on said refractive angles and said reflection angles, which transmission characteristic shows at least one of a minimum and a plateau and being dependent on the distance d, to a working point of the distance d, wherein the variation of the transmission around the working point is low, accordingly the derivation of the measured transmission characteristic is low.

11. The detection device of claim 10, wherein the distance d is set, based on a previously derived measurement of a transmission characteristic relying on said refractive angles and said reflection angles, which transmission characteristic shows at least one of a minimum and a plateau and being dependent on the distance d, to a working point of the distance d, wherein the variation of the transmission around the working point is low, accordingly the derivation of the measured transmission characteristic is low.

12. The detection device of claim 10, wherein said pattern is at least one selected from the group consisting of: an embosses pattern of helical shape, a rippled or ragged pattern, and an irregular pattern, wherein said pattern is aligned with the envelope.

13. The detection device of claim 10, wherein the envelope is made of a material such as an amorphous fluoropolymer or quartz that provides a total reflectance of the light inside said envelope.

14. The detection device of claim 10, wherein the envelope is coated with a reflecting substance which substance is a fluoropolymer or dye.

15. The detection device of claim 10, wherein the envelope has an longitudinal axis and wherein at least one of the first and the second waveguides is movable along said longitudinal axis.

16. The detection device of claim 10, wherein the end faces are spherically domed or lens shaped.

17. The detection device of claim 10, comprising a light source providing the light being emitted by the waveguide, said light source is at least one selected from the group consisting of: diode, diode array, incandescent lamp, deuterium lamp, mercury low-pressure or high-pressure discharge lamp, and any other suitable lamp.

* * * * *